United States Patent
Singh

(10) Patent No.: US 9,442,045 B2
(45) Date of Patent: Sep. 13, 2016

(54) MODEL-BASED LONGITUDINAL STIFFNESS ESTIMATION SYSTEM AND METHOD

(71) Applicant: The Goodyear Tire & Rubber Company, Akron, OH (US)

(72) Inventor: Kanwar Bharat Singh, Stow, OH (US)

(73) Assignee: The Goodyear Tire & Rubber Company, Akron, OH (US)

(*) Notice: Subject to any disclaimer, the term of this patent is extended or adjusted under 35 U.S.C. 154(b) by 308 days.

(21) Appl. No.: 14/244,384

(22) Filed: Apr. 3, 2014

(65) Prior Publication Data

US 2015/0285712 A1     Oct. 8, 2015

(51) Int. Cl.

| G01M 17/02 | (2006.01) |
|---|---|
| B60T 8/171 | (2006.01) |
| G01N 3/40 | (2006.01) |
| G01N 3/56 | (2006.01) |
| B60T 8/172 | (2006.01) |

(52) U.S. Cl.
CPC ............ *G01M 17/02* (2013.01); *B60T 8/171* (2013.01); *B60T 8/172* (2013.01); *G01N 3/40* (2013.01); *G01N 3/56* (2013.01); *B60T 2240/06* (2013.01); *B60T 2270/86* (2013.01)

(58) Field of Classification Search
CPC ....... B60T 8/172; B60T 8/171; G01M 17/02
See application file for complete search history.

(56) References Cited

U.S. PATENT DOCUMENTS

| 7,546,764 B2 | 6/2009 | Morinaga et al. ............... 73/146 |
|---|---|---|
| 7,552,628 B2 | 6/2009 | Mancosu et al. ............... 73/146 |
| 2004/0049303 A1 | 3/2004 | Levy et al. |
| 2004/0225423 A1 | 11/2004 | Carlson et al. |
| 2007/0112477 A1* | 5/2007 | Van Zanten .......... B60T 8/1725 701/2 |
| 2008/0103659 A1 | 5/2008 | Mancosu et al. ............... 701/41 |
| 2009/0055040 A1 | 2/2009 | Naguya ............... 701/29 |
| 2011/0199201 A1 | 8/2011 | Brusarosco et al. ........... 340/438 |
| 2012/0179327 A1 | 7/2012 | Yngve et al. |

FOREIGN PATENT DOCUMENTS

| DE | 102004032730 A1 | 2/2006 | |
|---|---|---|---|
| DE | 102007052751 A1 | 5/2009 | |
| EP | 1964736 A1 | 9/2008 | |
| EP | 2011/054363 | 5/2011 | ......... B60G 17/0165 |

OTHER PUBLICATIONS

European Search report received by Applicants Aug. 19, 2015.

Pages 1 through 29, "Slip-based Tire-road Friction Estimation" by Fredrik Gustafsson, Department of Electrical Engineering, Linköping University, Linkoping, Sweden. Nov. 28, 1996.

(Continued)

*Primary Examiner* — Paul West
(74) *Attorney, Agent, or Firm* — Edward T. Kennedy

(57) ABSTRACT

A tire-based system and method for estimating longitudinal stiffness between a tire and a road surface includes a longitudinal stiffness adaptation model for calculating longitudinal stiffness between a tire and a road surface from a plurality of scaling factors including the load level, the measured air cavity pressure of the one tire, and the measured temperature of the one tire compensated by a wear state estimation of the one tire. The wear state is obtained from a vehicle-measured vertical mode shift of the tire.

12 Claims, 19 Drawing Sheets

(56) References Cited

OTHER PUBLICATIONS

Pages 607 through 617, "Estimation of the Maximum Tire-road Friction Coefficient" by Steffen Müller, et al., Journal of Dynamic Systems, Measurement, and Control. Dec. 2003, vol. 125.

Page 454 through 458, "Real-time Slip-based Estimation of Maximum Tire-road Friction Coefficient" by Lee et al., IEFF/ASME Transactions on Mechatronics. Jun. 2004, vol. 9, No. 2.

"Experimental Analysis of Potentials for Tire Friction Estimation in Low-slip Operating Mode" by Pavkovi et al., reprinted from Vehicle Dynamics and Simulation 2006, SAE International, 400 Commonwealth Drive, Warrendale, PA 15096-0001. Apr. 306, 2006.

Pages 1, 2, 5 and 120 through 169, "Tire Modeling and Friction Estimation" by Jacob Svendenius, Department of Automatic Control, Lund University, Lund, Sweden. Apr. 2007.

Pages 3948 through 2953, "Robust Estimation of Road Friction Coefficient" by Ahn, et al. 2011 American Control Conference. Jun. 29 through Jul. 1, 2011.

Pages 1183 through 1195, Algorithms for Real-time Estimation of Individual Wheel Tire-road Friction Coefficients by Rajamani, et al., IEFF/ASME Transactions on Mechatronics. Dec. 2012, vol. 17, No. 6.

* cited by examiner

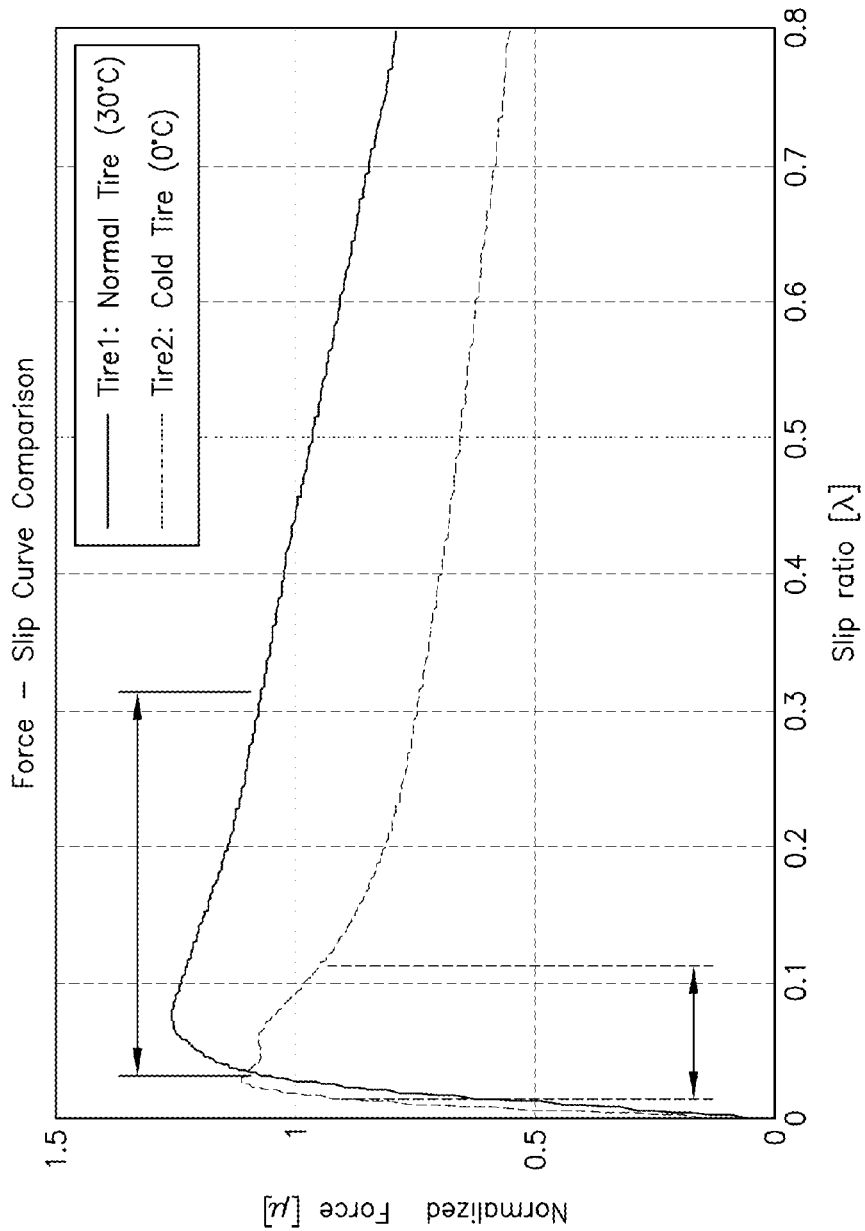

Road Friction Dependency

| | | Dry Braking | Wet Braking | % Change |
|---|---|---|---|---|
| 215/55R17 All Season | Stiffness | 49000 | 39718 | −18.942857 |
| | Grip | 0.985 | 0.752 | −23.654822 |
| 175/65R15 Summer | Stiffness | 42012 | 33787 | −19.57774 |
| | Grip | 1.1 | 0.86 | −21.818182 |
| 195/65R15 Summer | Stiffness | 52500 | 44000 | −16.190476 |
| | Grip | 0.99 | 0.71 | −28.282828 |
| 215/45R17 Summer | Stiffness | 73000 | 62000 | −15.068493 |
| | Grip | 1.18 | 0.86 | −27.118644 |

FIG-4

$$SL = \left[1 + q_{f1}\left[\frac{F_z - F_{z0}}{F_{z0}}\right]^2 + q_{f2}\frac{F_z - F_{z0}}{F_{z0}}\right] \cdot \left[1 + q_{f1}\left[\frac{P - P_0}{P_0}\right]\right]$$

Load and Pressure Adaptation $$ST = \left[1 + q_{t1}\frac{T - T_0}{T_0} + q_{t2}\left[\frac{T - T_0}{T_0}\right]^2\right]$$

Temperature Adaptation $$SW = \left[1 + q_w\left[\frac{W - W_0}{W_0}\right]\right]$$

Wear Adaptation $$C_x = \left[1 + q_{f1}\left[\frac{F_z - F_{z0}}{F_{z0}}\right]^2 + q_{f2}\frac{F_z - F_{z0}}{F_{z0}}\right] \cdot \left[1 + q_{f1}\left[\frac{P - P_0}{P_0}\right]\right] * \left[1 + q_{t1}\frac{T - T_0}{T_0} + q_{t2}\left[\frac{T - T_0}{T_0}\right]^2\right] * \left[1 + q_w\left[\frac{W - W_0}{W_0}\right]\right] \times C_0$$

Scaling Factors Introduced for Load, Pressure, Temperature, Wear Adaptation

FIG-5D

MODEL-BASED LONGITUDINAL STIFFNESS ESTIMATION SYSTEM AND METHOD

FIELD OF THE INVENTION

The subject invention relates generally to systems for estimating a road surface condition and, more specifically, to a model-based longitudinal stiffness estimation system and method useful in friction estimation.

BACKGROUND OF THE INVENTION

Real-time measurement or estimation of myriad road surface conditions are important and useful to vehicle control systems such as adaptive cruise control (ACC), anti-lock braking systems (ABS), electronic stability program (ESP) and acceleration slip regulation (ASR). Reliable and accurate road surface condition information is important for such systems to function as intended. One such road condition is surface friction. Typical road surface evaluation systems attempt to estimate road friction coefficients through estimation schemes that require certain levels of vehicle longitudinal and/or lateral motion excitations (e.g. accelerating, decelerating, and steering) and a persistence of such excitation levels in order to achieve a reliable friction estimation. While such schemes are valid in theory, attaining the requisite level and persistence of excitation to achieve a reliable friction estimation, however, has proven problematic in practice. Moreover, current schemes developed to estimate road surface friction ignore significant factors that can effect the accuracy of estimation.

Accordingly, an improved reliable and robust system and method for estimating road surface friction is desired for use in advanced vehicle control systems.

SUMMARY OF THE INVENTION

According to an aspect of the invention, a tire-based system and method for estimating longitudinal stiffness between a tire and a road surface is provided. The system includes one or more tire(s) mounted respectively to a wheel hub and supporting a vehicle, a load measurement scheme for determining a load level on the one tire, a wear estimator for estimating a wear state of the one tire and one or more tire-based sensor-derived input parameters. A longitudinal stiffness adaptation model calculates the longitudinal stiffness estimation scaled by the load level, the tire-based sensor input parameter(s), and the tire wear state.

According to another aspect of the invention, the tire-based sensor input parameter(s) are from the group: a measured air cavity pressure of the one tire; tire-specific construction characteristics of the one tire; a measured temperature of the one tire.

The system in yet another aspect includes a wear state estimator for generating a wear state estimation for the one tire(s) from a vehicle-measured acceleration of a hub supporting the one tire(s). The wear state estimator generates the wear state estimation from a detected a shift in a vertical mode of the one tire.

Pursuant to a further aspect, the longitudinal stiffness adaptation model algorithmically calculates the longitudinal stiffness estimation from compensating scaling factors including the load level, the measured air cavity pressure of the one tire, and the measured temperature of the one tire compensated by a wear state estimation of the one tire.

DEFINITIONS

"ANN" or "Artificial Neural Network" is an adaptive tool for non-linear statistical data modeling that changes its structure based on external or internal information that flows through a network during a learning phase. ANN neural networks are non-linear statistical data modeling tools used to model complex relationships between inputs and outputs or to find patterns in data.

"Aspect ratio" of the tire means the ratio of its section height (SH) to its section width (SW) multiplied by 100 percent for expression as a percentage.

"Asymmetric tread" means a tread that has a tread pattern not symmetrical about the center plane or equatorial plane EP of the tire.

"Axial" and "axially" means lines or directions that are parallel to the axis of rotation of the tire.

"CAN bus" or "controller area network" is a vehicle bus standard designed to allow microcontrollers and devices to communicate with each other within a vehicle without a host computer. CAN bus is a message-based protocol, designed specifically for automotive applications.

"Chafer" is a narrow strip of material placed around the outside of a tire bead to protect the cord plies from wearing and cutting against the rim and distribute the flexing above the rim.

"Circumferential" means lines or directions extending along the perimeter of the surface of the annular tread perpendicular to the axial direction.

"Equatorial Centerplane (CP)" means the plane perpendicular to the tire's axis of rotation and passing through the center of the tread.

"Footprint" means the contact patch or area of contact created by the tire tread with a flat surface as the tire rotates or rolls.

"Groove" means an elongated void area in a tire wall that may extend circumferentially or laterally about the tire wall. The "groove width" is equal to its average width over its length. A grooves is sized to accommodate an air tube as described.

"Inboard side" means the side of the tire nearest the vehicle when the tire is mounted on a wheel and the wheel is mounted on the vehicle.

"Kalman Filter" is a set of mathematical equations that implement a predictor-corrector type estimator that is optimal in the sense that it minimizes the estimated error covariance—when some presumed conditions are met.

"Lateral" means an axial direction.

"Lateral edges" means a line tangent to the axially outermost tread contact patch or footprint as measured under normal load and tire inflation, the lines being parallel to the equatorial centerplane.

"Luenberger Observer" is a state observer or estimation model. A "state observer" is a system that provide an estimate of the internal state of a given real system, from measurements of the input and output of the real system. It is typically computer-implemented, and provides the basis of many practical applications.

"Net contact area" means the total area of ground contacting tread elements between the lateral edges around the entire circumference of the tread divided by the gross area of the entire tread between the lateral edges.

"Non-directional tread" means a tread that has no preferred direction of forward travel and is not required to be positioned on a vehicle in a specific wheel position or positions to ensure that the tread pattern is aligned with the preferred direction of travel. Conversely, a directional tread pattern has a preferred direction of travel requiring specific wheel positioning.

"Outboard side" means the side of the tire farthest away from the vehicle when the tire is mounted on a wheel and the wheel is mounted on the vehicle.

"Peristaltic" means operating by means of wave-like contractions that propel contained matter, such as air, along tubular pathways.

"Piezoelectric Film Sensor" a device in the form of a film body that uses the piezoelectric effect actuated by a bending of the film body to measure pressure, acceleration, strain or force by converting them to an electrical charge.

"Radial" and "radially" means directions radially toward or away from the axis of rotation of the tire.

"Recursive least squares (RLS)" means an adaptive filter algorithm which recursively finds the filter coefficients that minimize a weighted linear least squares cost function relating to the input signals.

"Rib" means a circumferentially extending strip of rubber on the tread which is defined by at least one circumferential groove and either a second such groove or a lateral edge, the strip being laterally undivided by full-depth grooves.

"Sipe" means small slots molded into the tread elements of the tire that subdivide the tread surface and improve traction, sipes are generally narrow in width and close in the tires footprint as opposed to grooves that remain open in the tire's footprint.

"Slip Angle" is the angle between a vehicle's direction of ravel and the direction in which the front wheels are pointing. Slip angle is a measurement of the deviation between the plane of tire rotation and the direction of travel of a tire.

"Tread element" or "traction element" means a rib or a block element defined by having a shape adjacent grooves.

"Tread Arc Width" means the arc length of the tread as measured between the lateral edges of the tread.

BRIEF DESCRIPTION OF THE DRAWINGS

The invention will be described by way of example and with reference to the accompanying drawings in which:

FIGS. 3A through 3D are force-slip curve comparison graphs comparing normal to cold tires; new to worn tires; high inflated to low inflated tires; and summer to all season tires, respectively.

FIG. 4 is a table summarizing road friction dependency for four tires under dry braking and wet braking conditions.

FIG. 5D is a representation of the expressions for load and pressure adaptation, temperature adaptation, and wear adaptation and their use as scaling expressions in a model based longitudinal (stiffness) estimation.

DETAILED DESCRIPTION OF THE INVENTION

Accurate estimation of tire-road friction has utility in the implementation of vehicle control systems. Estimation methods can be categorized into "cause-based" and "effect-based" approaches according to the fundamental phenomena. "Cause-based" strategies try to measure factors that lead to changes in friction and then attempt to predict what friction change will be based on past experience or friction models. "Effect-based approaches, on the other hand, measure the effects that friction has on the vehicle or tires during driving. They attempt to extrapolate what the limit friction will be based on this data.

The measurement of vehicle motion itself may be used to obtain an estimate of the tire-road friction coefficient. Two types of systems may be employed: systems that utilize longitudinal vehicle dynamics and longitudinal motion measurements and systems that utilize lateral vehicle dynamics and lateral motion measurements. The lateral system can be utilized primarily while the vehicle is being steered while a longitudinal motion-based system is applicable generally during vehicle acceleration and deceleration.

Figure 1:
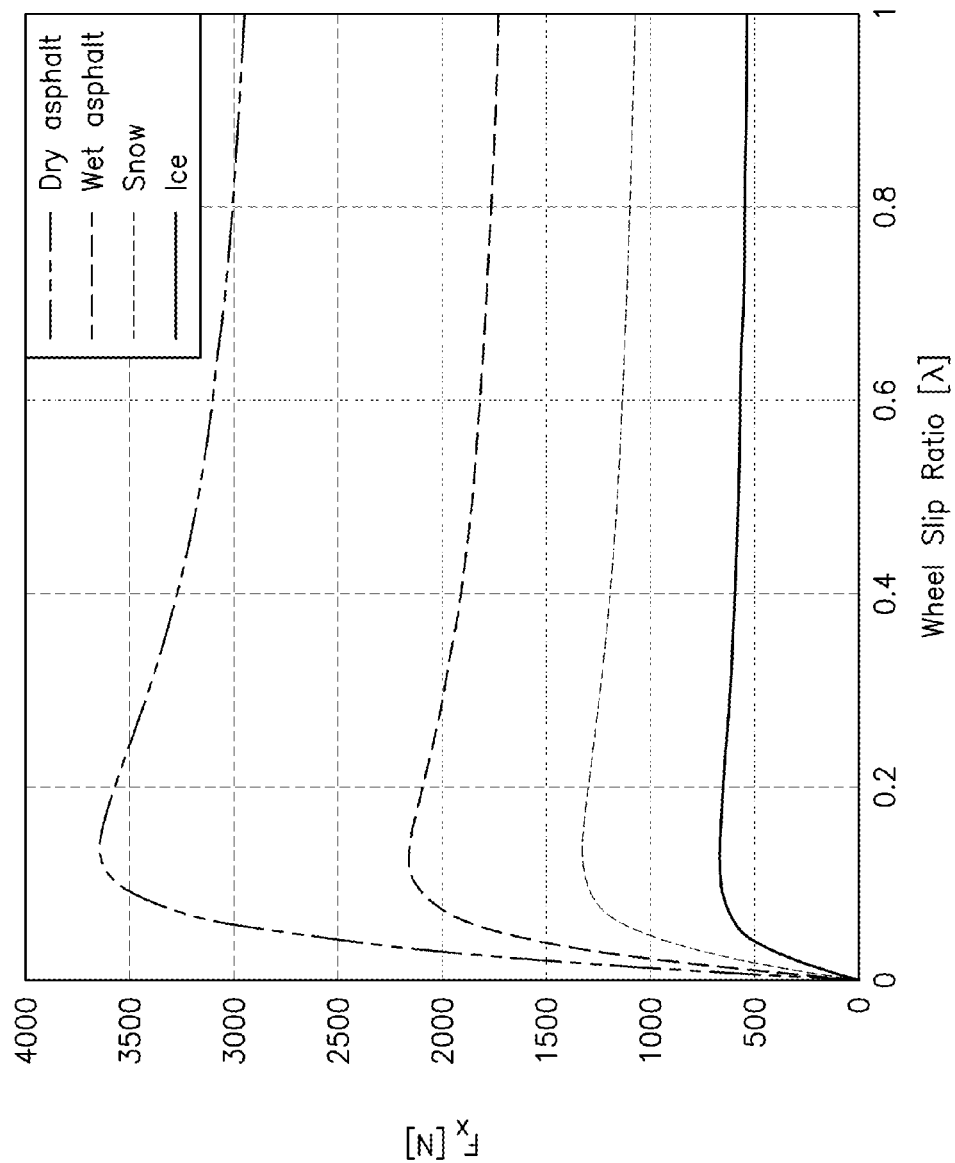
FIG. 1 is a graph showing tire longitudinal stiffness vs. wheel slip ratio for four types of road surface conditions.
Figure 2:
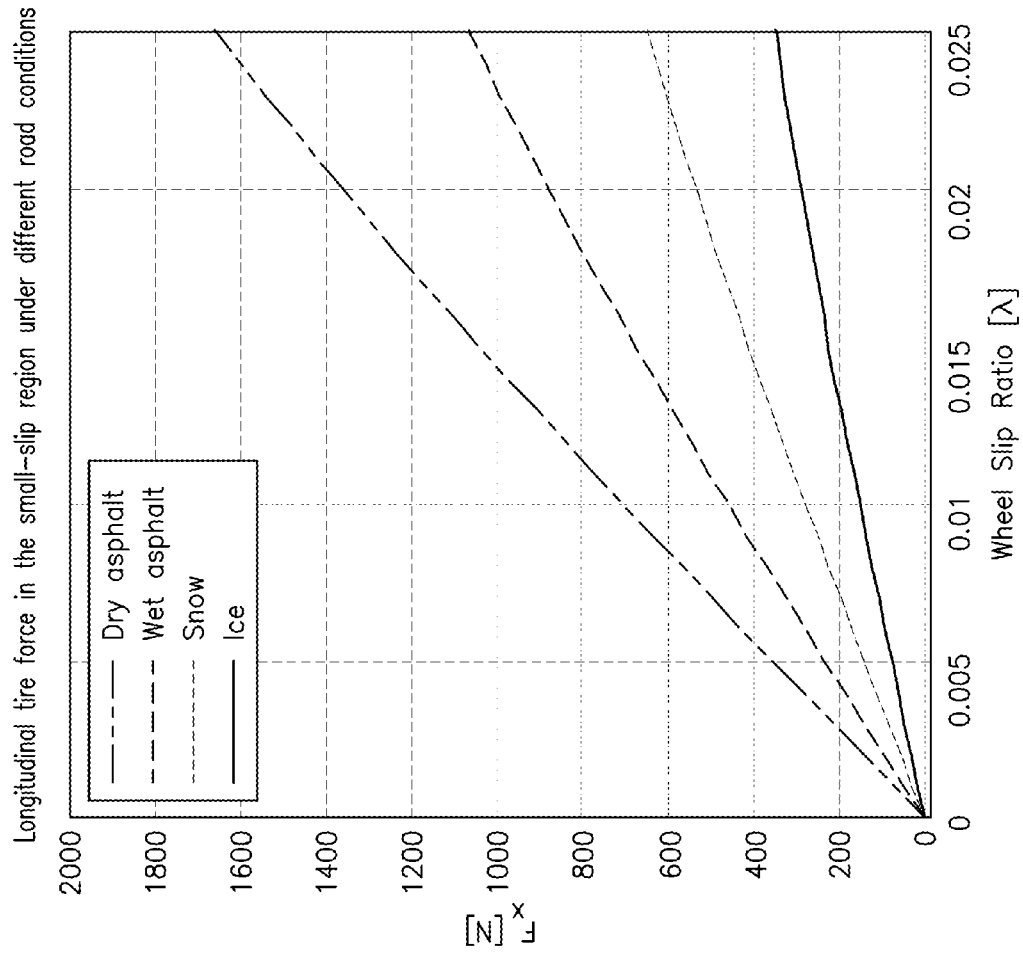
FIG. 2 is a graph of tire longitudinal stiffness vs. wheel slip ratio in the small-slip region of the graph of FIG. 1.

An approach to assess the friction of a road-surface is to estimate the longitudinal stiffness, i.e. the incline of the tire force relative to slip and from this value distinguish between different surface conditions. FIG. 1 shows a graph of longitudinal stiffness $F_x[N]$ vs. wheel slip ratio $[\lambda]$ for different road surface conditions. FIG. 2 shows an enlarged low slip region of the graph of FIG. 1. As will be noted, the incline of the tire force relative to slip at low slip regions of the curves makes deriving a maximum friction coefficient problematic from the value of slip-slope alone. The subject invention therefore presents a system and method of estimating the friction coefficient using the slip-slope method but adapts a slip-slope approach to incorporate important parameters that govern tire longitudinal stiffness behavior in the low slip region. Parameters included in the estimation adaptation include tire inflation pressure, tread depth (tire wear condition), normal loading, tire construction and temperature. Such parameters are measured from tire-based sensors and are used to compensate for dependencies of pressure, temperature, wear state, tire construction on friction estimation.

Figure 3B:
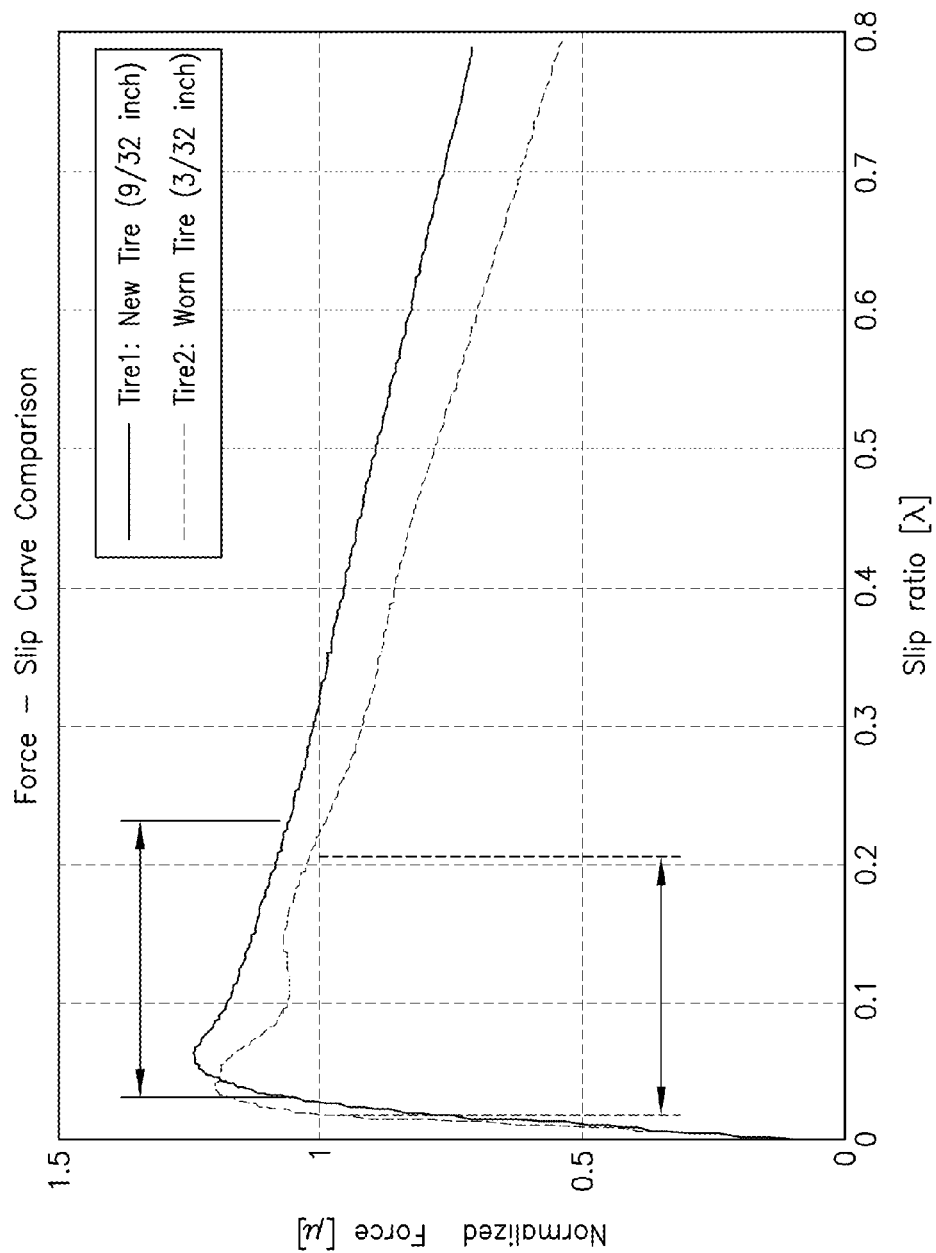
Figure 3C:
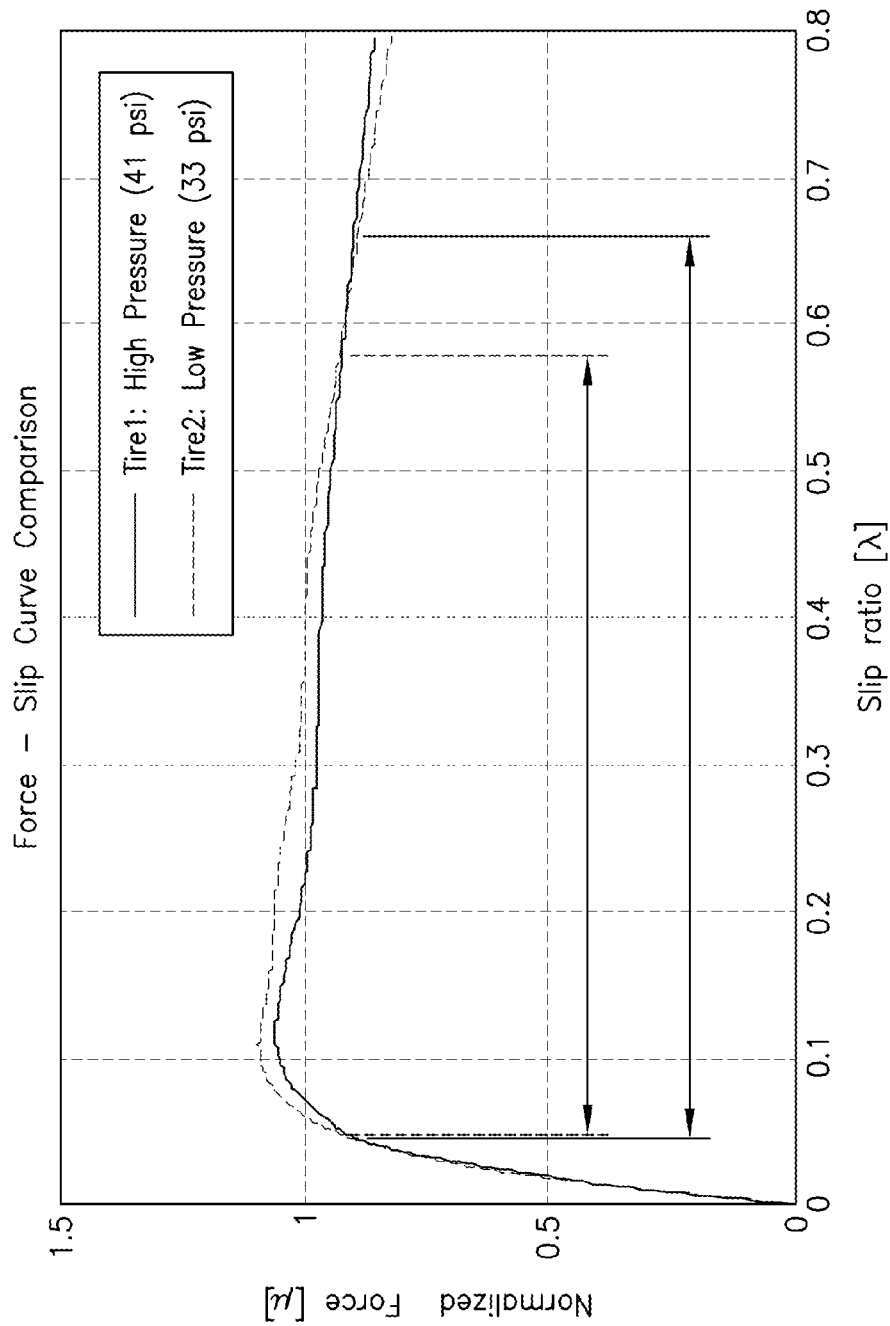
Figure 3D:
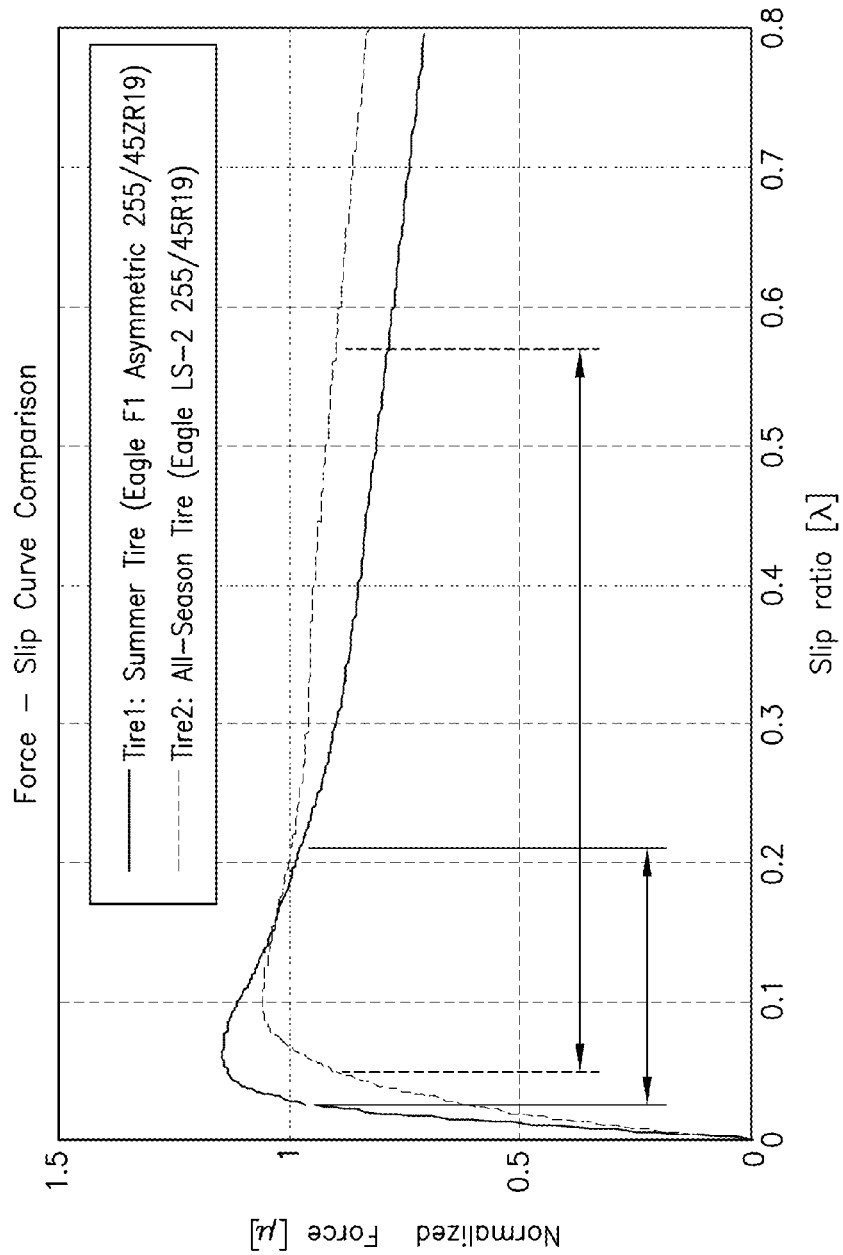

FIGS. 3A through 3D demonstrate how significant such tire-based parameters are to a determination of longitudinal force in the low slip region of the curves. The graph of FIG. 3 validates that tire temperature affects the force-slip curve, comparing the curves of a normal tire 1 at 30° C. to a cold tire 2 at 0° C. FIG. 3B shows tire wear dependency in comparing new tire tread depth to a worn tire tread depth. FIG. 3C shows the force-slip curve comparison between a high inflation pressure tire at 41 psi and a low inflation pressure tire at 22 psi. FIG. 3D confirms the dependency of the force-slip curve in a low slip region on tire construction, comparing a Goodyear Eagle F1 tire to an All-Season Eagle tire. A summary of the test results comparing the tires is presented in tabular form in FIG. 4. As will be seen, the percentage change between wet braking and dry braking is significant and varies between tires of differing construction.

The following generalizations may be drawn from the test results reflected in FIGS. 3A through 3D. As compared to a normal tire at 30° C., the cold tire has 40 to 45 percent higher braking stiffness. As compared to a tire at a higher pressure, the tire at a lower pressure has a slightly lower braking stiffness. As compared to a new tire, the worn tire has 30 percent higher braking stiffness. As compared to a summer tire, an all season tire has a dramatic effect on the braking stiffness. Finally, as summarized in FIG. 4, there is noted a 15 percent drop in stiffness during wet conditions. The load on a tire thus has a moderate effect on longitudinal stiffness ($C_x$), about 10 percent per 100 pounds; tire inflation pressure has a relatively small dependence; tire wear state has a high dependency, about 30 percent in new vs. worn; tire temperature has a high dependency, about 45 to 50 percent in a cold tire vs. normal temperature tire; and road surface type (friction) has a high dependency, about 10 to 15 percent in dry vs. wet and 90 percent in dry vs. ice. The conclusion to be drawn is that a tire's slip slope is different based on the factors above. Thus, the subject system and methodology does not use only the value of the slip slope itself but, rather, employs factor adaptation models to compensate for the inflation pressure, tread depth, normal loading and temperature dependencies.

Figure 5A:
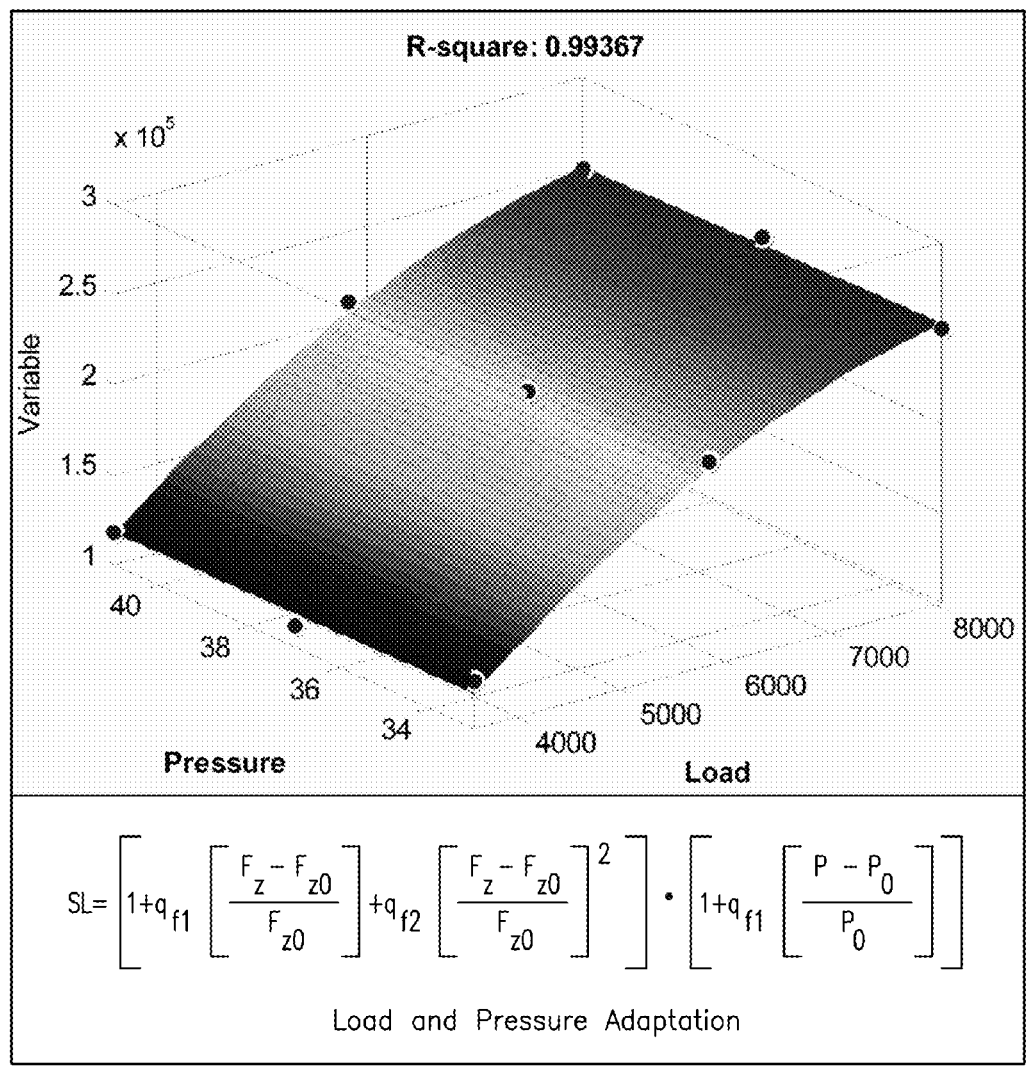
FIG. 5A is a graph showing lad and pressure dependency and a load and pressure adaption algorithm adjusting for the dependency in longitudinal stiffness calculation.
Figure 5B:
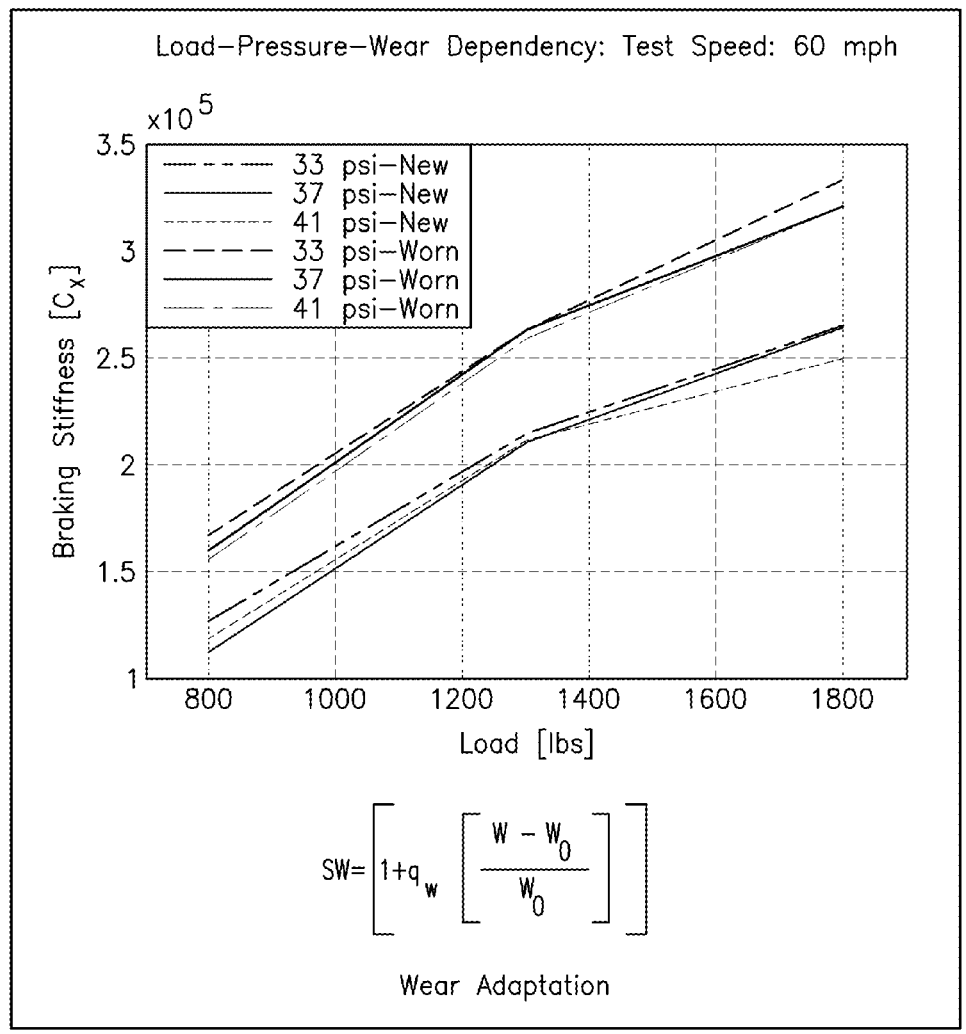
FIG. 5B is a test result graph showing load-pressure-wear dependency at 60 mph for new and worn tires at different inflation pressures. The graph shows braking stiffness vs. load and provides a wear adaption algorithm adjusting for the wear dependency in a stiffness calculation.
Figure 5C:
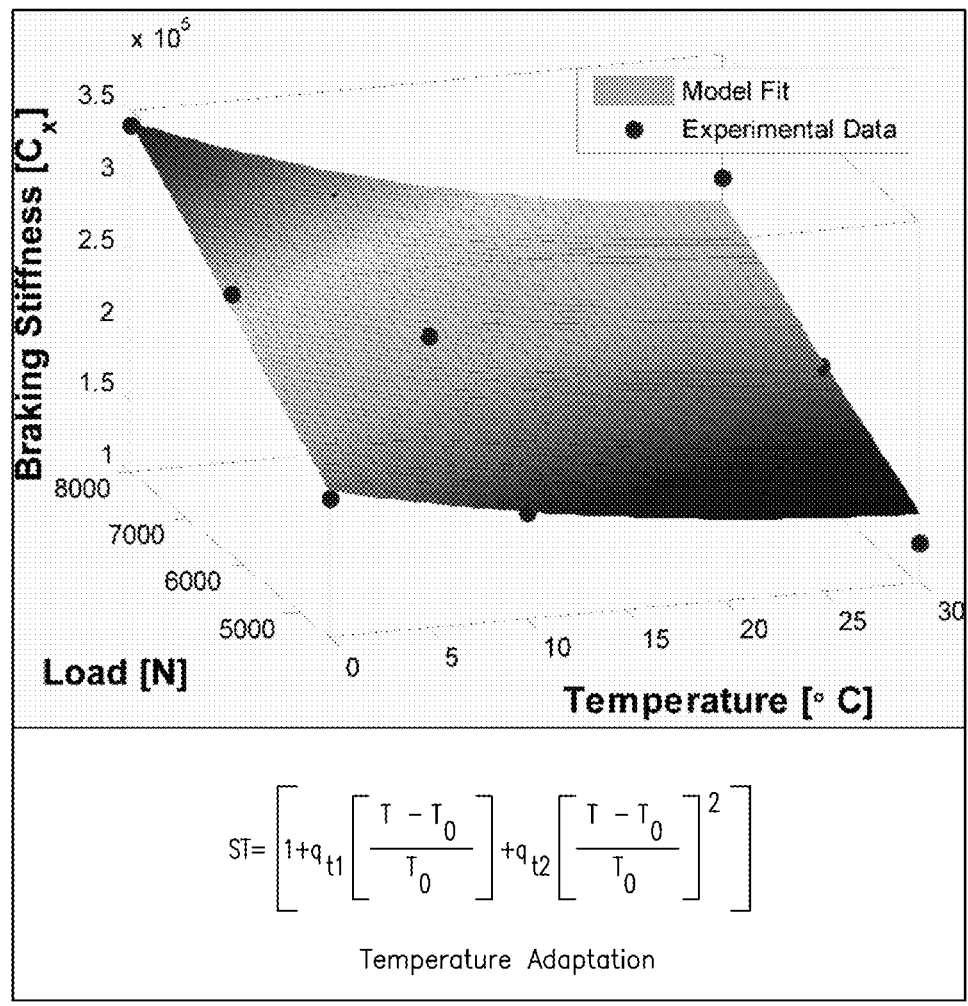
FIG. 5C is a graph showing dependency of braking stiffness to load and temperature and representing an expression adapting stiffness to temperature.
Figure 6:
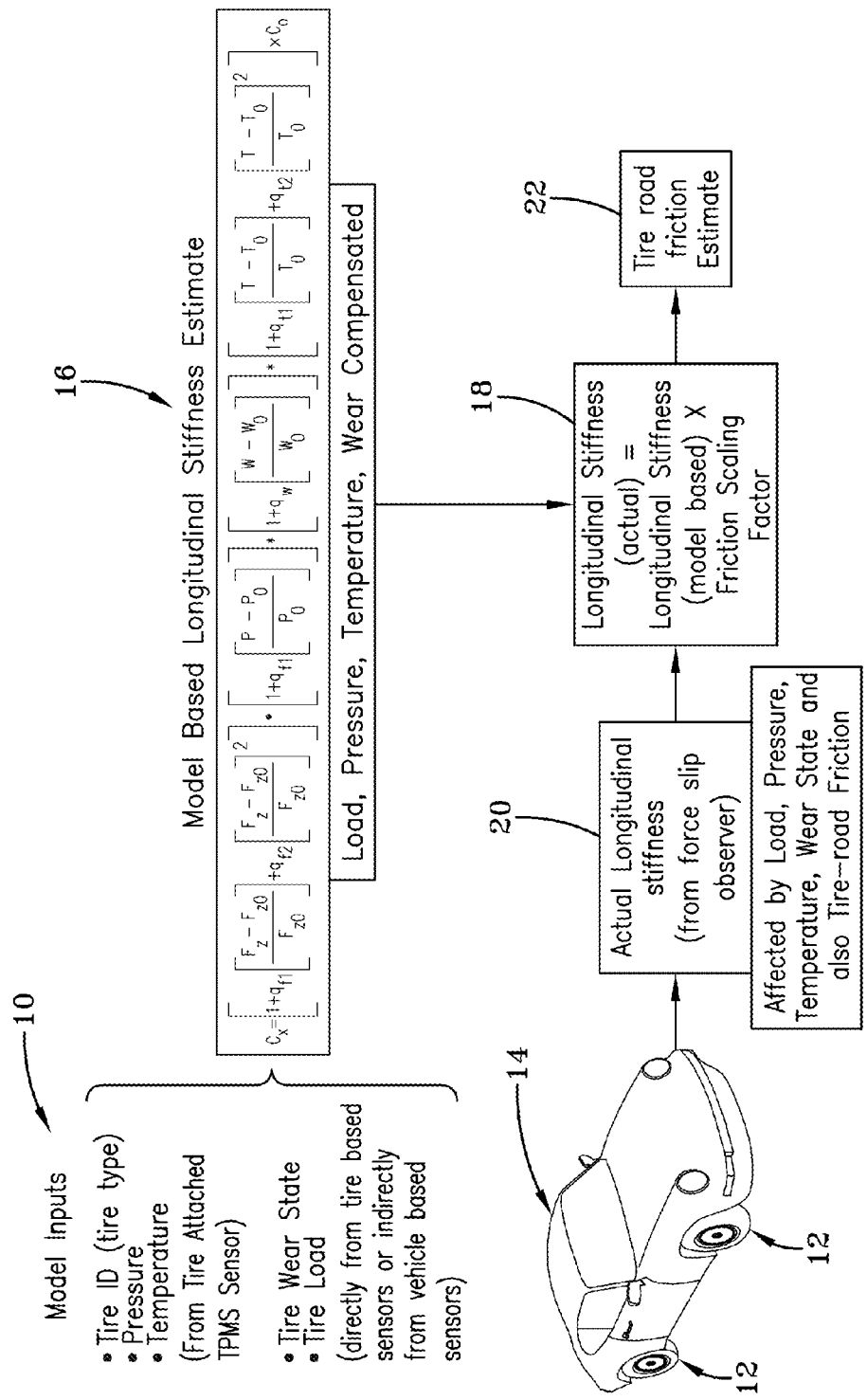
FIG. 6 is a schematic representation of the friction estimate system and method.

FIGS. 5A through 5C shows the adaptation and compensation models for load and pressure, wear, temperature. In FIG. 5A. adaptation model for SL attributed to load and pressure is shown by first order in pressure and second order in load components, in which SL=load and pressure adaptation factor
Fz=load
$Fz_o$=nominal load
P=pressure
$P_o$=nominal pressure
$q_f$=model scaling coefficients for load
$q_p$=model scaling coefficients for pressure Wear adaptation is represented in the expression for SW shown in FIG. 5B in which:

SL=wear state adaptation factor
W=tread depth
$W_o$=nominal tread depth
$q_w$=model scaling coefficients for the tire wear state In FIG. 5C the braking stiffness adaptation model is indicated by the expression for ST in which:

ST=temperature adaptation factor
T=tire temperature
$T_o$=nominal tire temperature
$q_t$=model scaling coefficients for tire temperature The load, pressure, wear, and temperature adaptations embodied within the model expressions of FIGS. 5A through 5C are integrated into the scaled stiffness under actual operating conditions $C_x$ model shown in FIG. 5D. FIG. 6 is a schematic representation of the friction estimate system and method. Referring to FIG. 6, tire-based model inputs 10 consist of tire ID (used to identify tire type and construction), pressure and temperature are obtained from sensors within a tire-attached TPMS module. One or more TPMS modules are mounted to each tire 12 supporting vehicle 14. The TPMS modules (not shown) may be mounted to an inner liner of the tires by conventional means such as an adhesive. Each TPMS module through commercially available sensors monitors tire pressure and temperature and contains stored data identifying the tire. The data from each TPMS module may be transmitted wirelessly to a data processor for stiffness estimation. In addition, further tire-based inputs 10 into the adaptation model for deriving a Model-based Longitudinal Stiffness Estimation 16 include tire wear state and tire load, available from tire-based sensors or indirectly from vehicle based sensors.

An Actual Longitudinal Stiffness Estimation 20 is determined from a force slip observer and is affected by load, pressure, temperature, wear state and tire-road friction. The Actual Longitudinal Stiffness Estimation 20 is derived from vehicle-based inputs available sensors on commercially available vehicles. The vehicle-based Actual Longitudinal Stiffness Estimation 20 and the model-based Longitudinal Stiffness Estimation 16 are used in the algorithm 18 which conducts a recursive least square estimation with forgetting factor analysis and outputs the tire road friction estimate 22 sought. The friction scaling factor used in the RLS Estimation With Forgetting Factor is a direct measure of the tire road friction coefficient. It will be appreciated that the Actual Longitudinal Stiffness Estimation 20 utilizes a force slip observer. The Model-based Longitudinal Stiffness Estimate 16 employs the algorithm identified and considers dry road condition as the reference condition.

Figure 7:
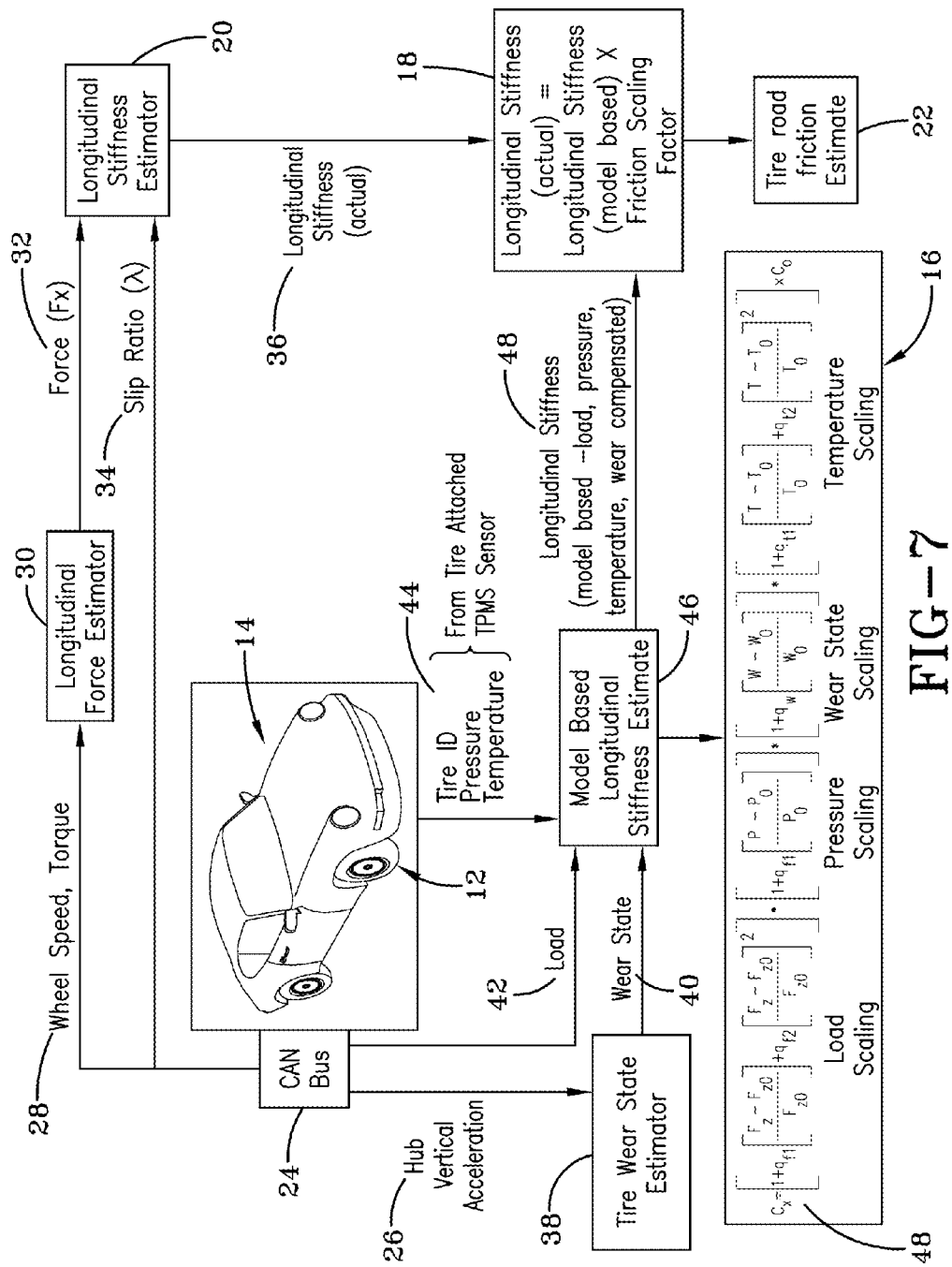
FIG. 7 is an on-vehicle implementation flowchart of the friction estimate system and method showing the integration of actual and model-based stiffness calculations in the tire road friction estimate.

The on-vehicle implementation flowchart of the FIG. 6 system and method is shown in FIG. 7. As explained, the vehicle 14 is shown as a passenger car but may be any type of vehicle carried by tires 12. Tires 12 are each equipped with a mounted TPMS module (not shown) from which inputs 44 (tire ID, pressure, temperature) from each tire are sensor generated. The vehicle 14 is equipped with a CAN bus (controller area network) and on-vehicle sensors that generate measurement of hub vertical acceleration 26, slip ratio 34, wheel speed and torque 28, and measurement of vehicle load 42. The wheel speed and torque 28 are used to produce a longitudinal force estimation $F_x$ 42 using a sliding mode observer (SMC). The longitudinal force estimation $F_x$ 42 is input with the slip ratio 34 into a longitudinal stiffness estimation model 20 that utilizes a recursive least square (RLS) with forgetting factor algorithm. From the longitudinal stiffness estimator 20 a longitudinal stiffness (actual) computation 36 is made.

The model-based longitudinal estimation 46 proceeds as follows. From on-board vehicle sensors a hub vertical acceleration is accessed from CANbus24. The hub vertical acceleration 26 is input into a tire wear state estimator. Such an estimator system and method is disclosed in pending U.S. patent application Ser. No. 13/917,691 filed Jun. 14, 2013, hereby incorporated by reference herein. From estimator 38, a wear state estimation 40 is made and used as an input with a vehicle-based measurement of vehicle load 42 into the model based longitudinal stiffness estimation 46. Tire-based inputs 44 are likewise input into the estimation 46, the inputs 44 including a tire ID (used to identify tire-specific structural composition), tire cavity pressure and tire liner temperature. The vehicle-based inputs of wear state 40 and load 42, together with tire-based inputs 44 of tire ID, pressure, and temperature, are applied within the adaptation model 16 described above in regard to FIG. 6. Coefficients in the expression in FIG. 6 are tire specific. A tire specific empirically generated database is constructed for each tire using the subject system. Once the tire ID is determined, it is used to consult the database and retrieve tire specific coefficients to be used in the model-based calculation of $C_x$. The load scaling, pressure scaling wear state scaling and temperature scaling components to algorithm 16 yield an acceptably accurate compensated model-based estimation of the longitudinal stiffness $C_x$ 48.

The model is given in FIG. 7 at numeral 16 wherein:
$C_o$=Stiffness under nominal operating conditions
$C_x$=Scaled stiffness under actual operating conditions The compensated model-based longitudinal stiffness estimate Cx is input with the longitudinal stiffness (actual) measurement 20 based on actual vehicle-based inputs of force ($F_x$) and slip ratio ($\lambda$) into a Recursive Least Square Estimation With Forgetting Factor Algorithm 18 as shown. The longitudinal stiffness (actual) from vehicle-based sensors is compared with the longitudinal stiffness estimation 48 (model based-load, pressure, temperature, wear compensated) and the difference between the two longitudinal stiffness estimations attributed to tire road friction 22. The estimation of tire road friction 22 thus utilizes both a model-based tire-input compensated longitudinal stiffness estimation and a vehicle-based estimation of longitudinal stiffness to achieve a more accurate estimation.

The on-vehicle estimation of tire longitudinal force ($F_x$) is achieved by an estimation algorithm derived as follows. The dynamic equation of the angular motion of a wheel is give as:

$$J\dot{\omega}_w = (T_w - T_b) - F_x r_w - F_{rr} r_w$$

J: wheel inertia
$\omega_w$: wheel speed
$T_w$=drive torque
$T_w$: brake torque
$F_x$: longitudinal force
$r_w$: tire rolling radius
$F_{rr}$: tire rolling resistance force Where the subscripts have been omitted for convenience. The same estimator and equations hold for all the wheels. Rearranging Equation (3.14) yields an expression for the longitudinal force as:

$$F_x = \frac{(T_w - T_b) - J\dot{\omega}_w}{r_w} - F_{rr}$$

Here, the wheel drive torque can be estimated by using the turbine torque, the turbine angular velocity, and the wheel angular velocity. It is assumed that the brake pressure of each wheel is an available signal. Therefore, the brake torque can be computed by the brake gain. The wheel rolling resistance force is given by the expression:

$$F_{rr} = 0.005 + 3.24 \cdot 0.01 \cdot (r_w \cdot \omega_w)^2$$

The accuracy of longitudinal force estimation using the above equation depends on the accuracy of the effective tire radius. Obtaining an accurate estimate of effective tire radius may be determined as:

$$r_{w,i} = r_o - \frac{F_{z,i}}{k_t}$$

$r_o$: rolling radius at nominal load
$r_{w,i}$=rolling radius at operating load
$F_{z,i}$: operating tire load
$k_t$: tire vertical stiffness Even though the above equation is a relatively simple (open-loop) method to estimate the longitudinal tire force $F_x$ (i.e. the longitudinal force may be calculated directly using the equation 3.15, or by use of a recursive least squares (RLS) method for a smoother estimation), finding the time derivative of angular wheel speed signals in real-world conditions can pose challenges. To avoid the need to take the derivatives of angular wheel speed signals, a sliding mode observer (SMO) based estimation scheme may be used. The SMO uses a sliding mode structure, with the state estimate evolving according to the wheel dynamics model (ref. Eq. (3.14)), the force model, and the sign of the measurement estimation error.

$$J\dot{\hat{\omega}}_w = (T_w - T_b) - \hat{F}_x r_w - F_{rr} r_w + k_1 sgn(\omega_w - \hat{\omega}_w)$$

$$\dot{\hat{F}}_x = k_2 sgn(\omega_w - \hat{\omega}_w)$$

Here $k_1$ & $k_2$ are the observer gains and sgn($\cdot$) denotes signum function defined as:

$$sgn(s(t)) = \begin{cases} 1, & \text{if } s(t) > 0 \\ 0, & \text{if } s(t) = 0 \\ -1, & \text{if } s(t) < 0 \end{cases}$$

Figure 8A:
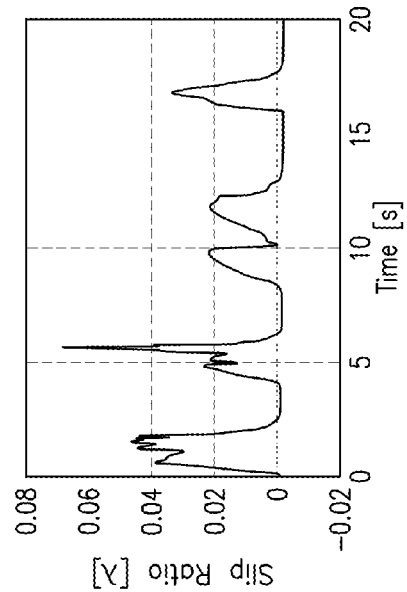
FIGS. 8A through 8C are validation graphs showing SMC Observer Based longitudinal force estimation over time in a test sequence vs. actual.
Figure 8B:
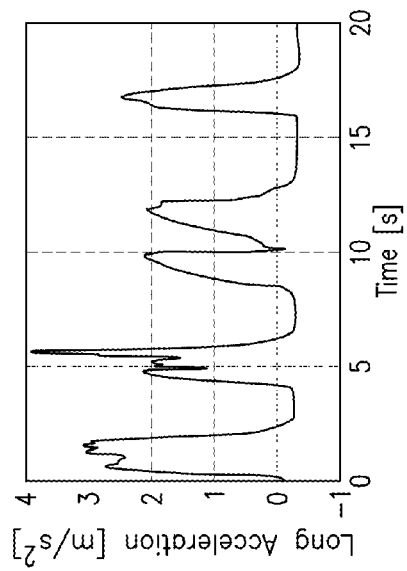
Figure 8C:
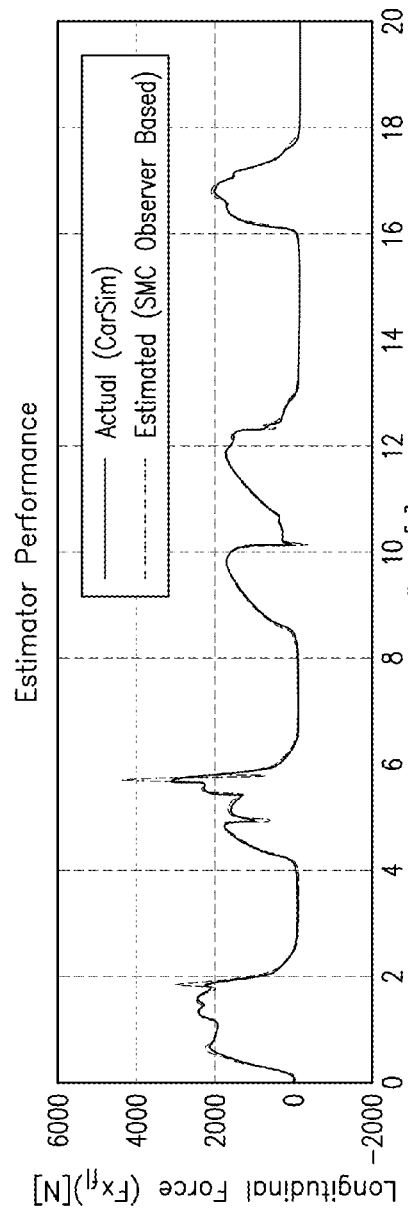

A validation of the subject system and method was conducted and the results are reflected in the graphs of FIGS. 8A, 8B, 8C). The proposed SMC based longitudinal force estimation algorithm was evaluated in simulations by implementing it in CARSIM, an industry standard vehicle dynamics simulation software. The vehicle maneuver is straight driving with intermittent gas pedal presses. In FIG. 8A, the longitudinal acceleration is plotted over time, FIG. 8B the slip ratio, and FIG. 8C the longitudinal force (actual (Car Sim) and Estimated (SMC Observer Based)). The results show that the estimated longitudinal forces closely match the simulated forces. Also, the estimated forces converge quickly to the simulated forces.

The longitudinal force model in the small-slip range can be expressed as follows:

$$F_x = C_x \cdot \lambda, \text{ for } |\lambda| < 3\%$$

Satisfactory performance of the wheel dynamics based observer in the small slip region ($|\lambda| < 3\%$) provides us with an opportunity to adaptively estimate the longitudinal stiffness of the tire using an on-line parameter estimation algorithm. Above equation can be rewritten into a standard parameter identification form as follows:

$$y(t) = \phi^T(t) \cdot \theta(t)$$

where y(t)=$F_x$ is the system output (from the wheel dynamics based observer), $\theta(t)=C_x$, is the unknown parameter, and $\phi^T(t)=\lambda$ is the measured slip ratio. The unknown parameter $\theta(t)$ can be identified in real-time using parameter identification approach.

The recursive least squares (RLS) algorithm provides a method to iteratively update the unknown parameter at each sampling time to minimize the sum of the squares of the modeling error using the past data contained within the regression vector, $\phi(t)$. The procedure or solving the RLS problem is as follows:

Step 0: Initialize the unknown parameter $\theta(0)$ and the covariance matrix $P(0)$; set the forgetting factor $\lambda$.

Step 1: Measure the system output $y(t)$ and compute the regression vector $\phi(t)$.

Step 2: Calculate the identification error $e(t)$:

$$e(t)=y(t)-\phi^T(t)\cdot\theta(t-1)$$

Step 3: Calculate the gain $k(t)$:

$$k(t)=P(t-1)\phi(t)[\lambda+\phi^T(t)P(t-1)\phi(t)]^{-1}$$

Step 4: Calculate the covariance matrix:

$$P(t)=(1-k(t)\phi^T(t))\lambda^{-1}P(t-1)$$

Step 5: Update the unknown parameter:

$$\theta(t)=\theta(t-1)+k(t)e(t)$$

Step 6: Repeat Steps 1 through 5 for each time step.

Figure 9A:
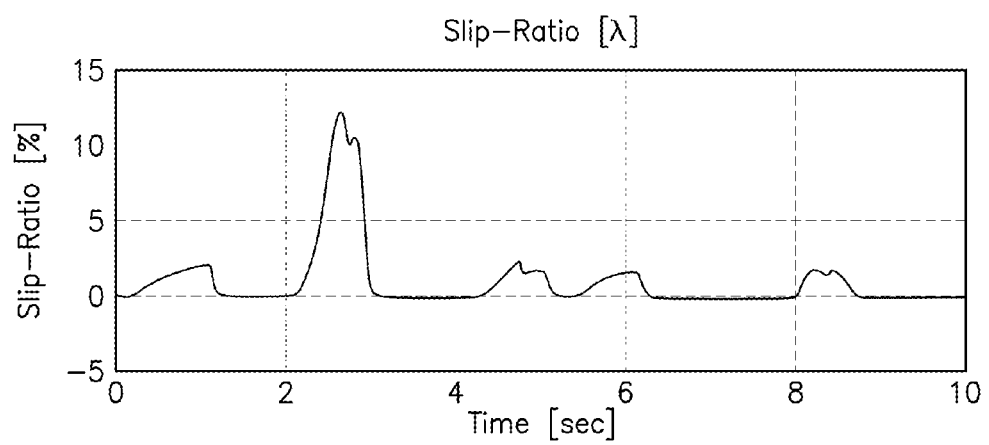
FIG. 9A is a graph showing validation of on-vehicle estimation of tire slip ratio over time.
Figure 9B:
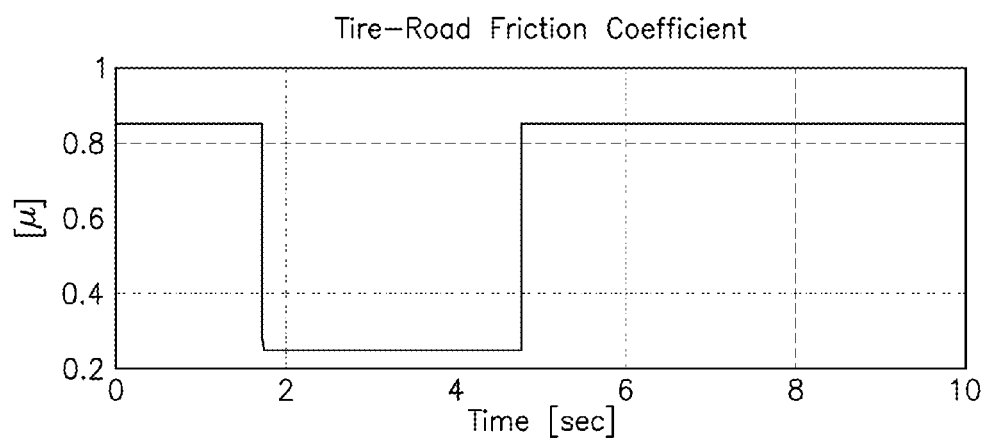
FIG. 9B is a graph showing tire-road friction coefficient estimation over time.
Figure 9C:
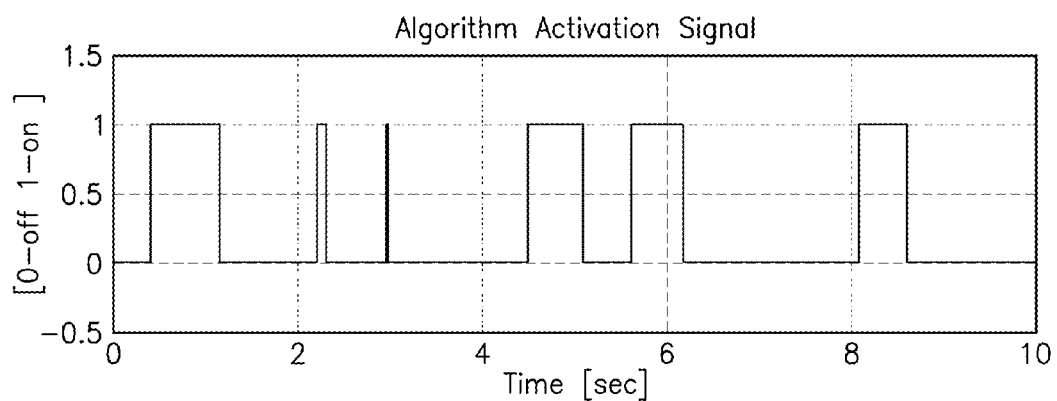
FIG. 9C shows a graph of algorithm activation signal.
Figure 9D:
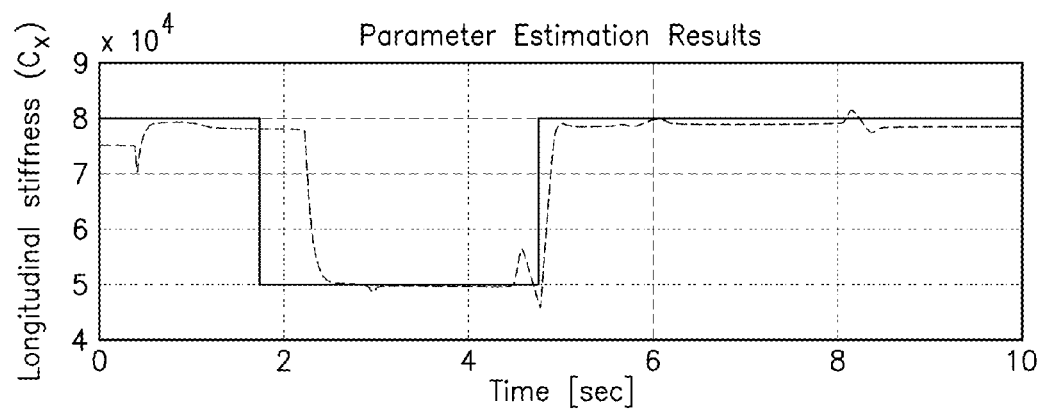
FIG. 9D shows a graph of estimation results of longitudinal stiffness over time.

In FIGS. 9A through 9D, experimental validation graphs are shown. The performance of the RLS based tire longitudinal stiffness estimation algorithm is evaluated with simulations where the road surface is designed to have sudden friction coefficient changes, and the vehicle maneuver is straight driving with intermittent gas pedal presses. In FIG. 9A, slip ratio (percent) over time is graphed, and in FIG. 9B, tire-road friction coefficient over time is shown. FIG. 9C shows the algorithm activation signal and FIG. 9D the parameter estimation results, graphing longitudinal stiffness ($C_x$) for both actual and estimated values. It can be seen that the estimator shows delayed estimation at the first change due to lack of excitation at that time. Once excitation occurs at 2.2 seconds, the estimator updates the longitudinal stiffness. The results confirms that estimated longitudinal stiffness (broken line) closely matches actual (solid line).

Figures 10A, 10B:
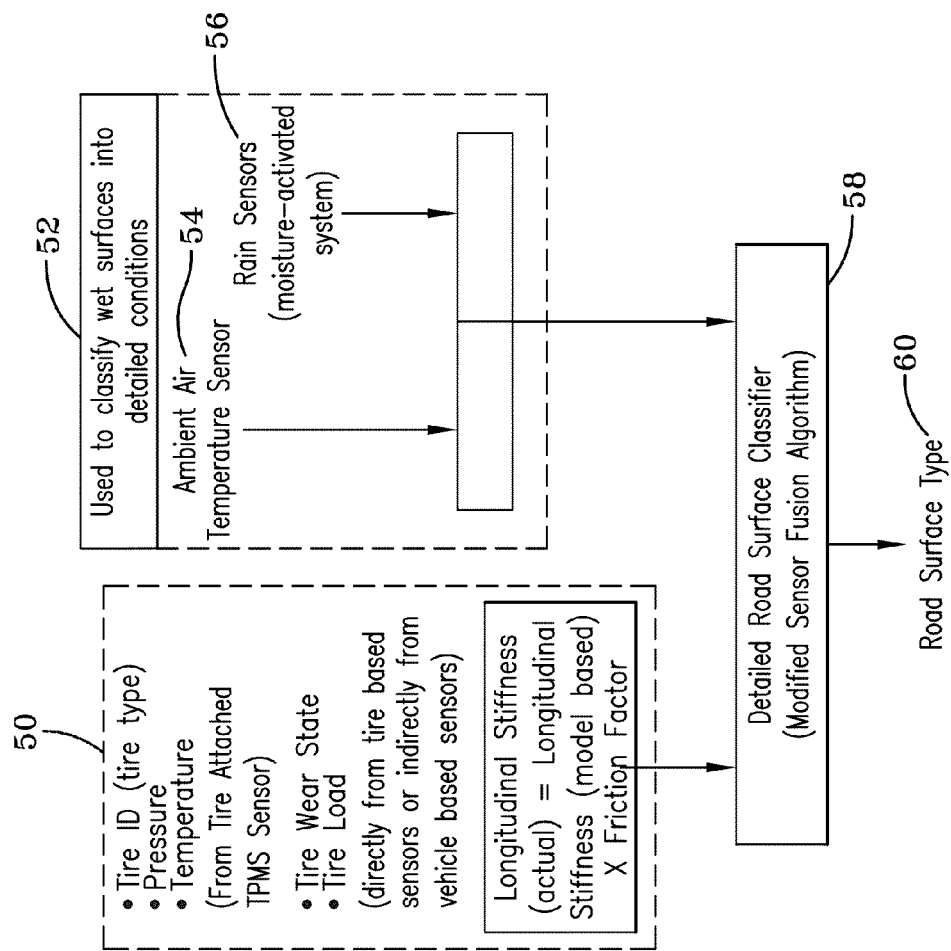
FIG. 10A is a flow chart of the use of friction estimation and air temperature and moisture inputs into a detailed road surface classifier.
FIG. 10B is a table showing the classes of road surface.

FIGS. 10A and 10B show a schematic block diagram of how the above friction estimation may be used in a sensor fusion approach for improved road surface classification. As explained above, tire-based inputs of tire ID, pressure and temperature are obtained from a tire-based TPMS Sensor Module. The tire wear state and tire load inputs are derived, either directly from tire sensors or indirectly from vehicle based sensors, and with the tire-based inputs, are used to compute the friction estimation from the expression: longitudinal stiffness (actual)=longitudinal stiffness (model based) X Friction Factor. Block 50 represents a summary of the friction estimation step.

In order to classify wet surfaces into a detailed condition analysis 52, temperature sensors are used to detect ambient air temperature 54 and rain sensors 56 are used to detect moisture in a moisture activated system 56. Both air temperature and moisture sensor inputs with the friction estimate 22 from the system and method described previously in reference to FIG. 7 are inputs into a detailed road surface classifier 58 in the form of a Modified Sensor Fusion Algorithm.

From the Modified Sensor Fusion Algorithm, a Road Surface Type is determined. The table in FIG. 10B shows a comparison between basic surface types and the surface types determined from the Modified Sensor Fusion Algorithm approach.

Figure 11:
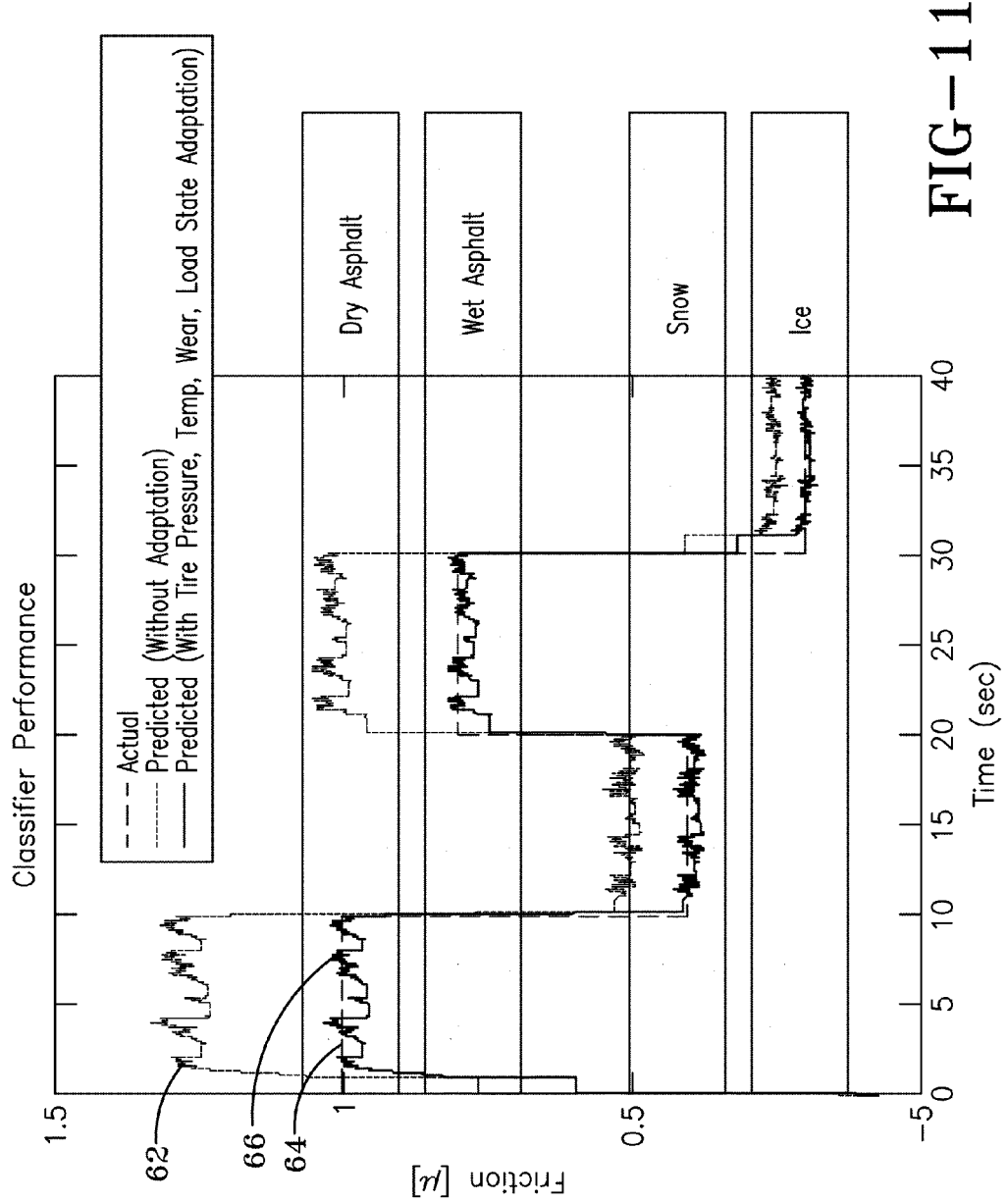
FIG. 11 is a graph of road surface classifier performance showing actual vs. predicted (with and without wear state adaptation) friction estimation comparison and showing the resultant misclassification (without tire wear compensation).
Figure 12:
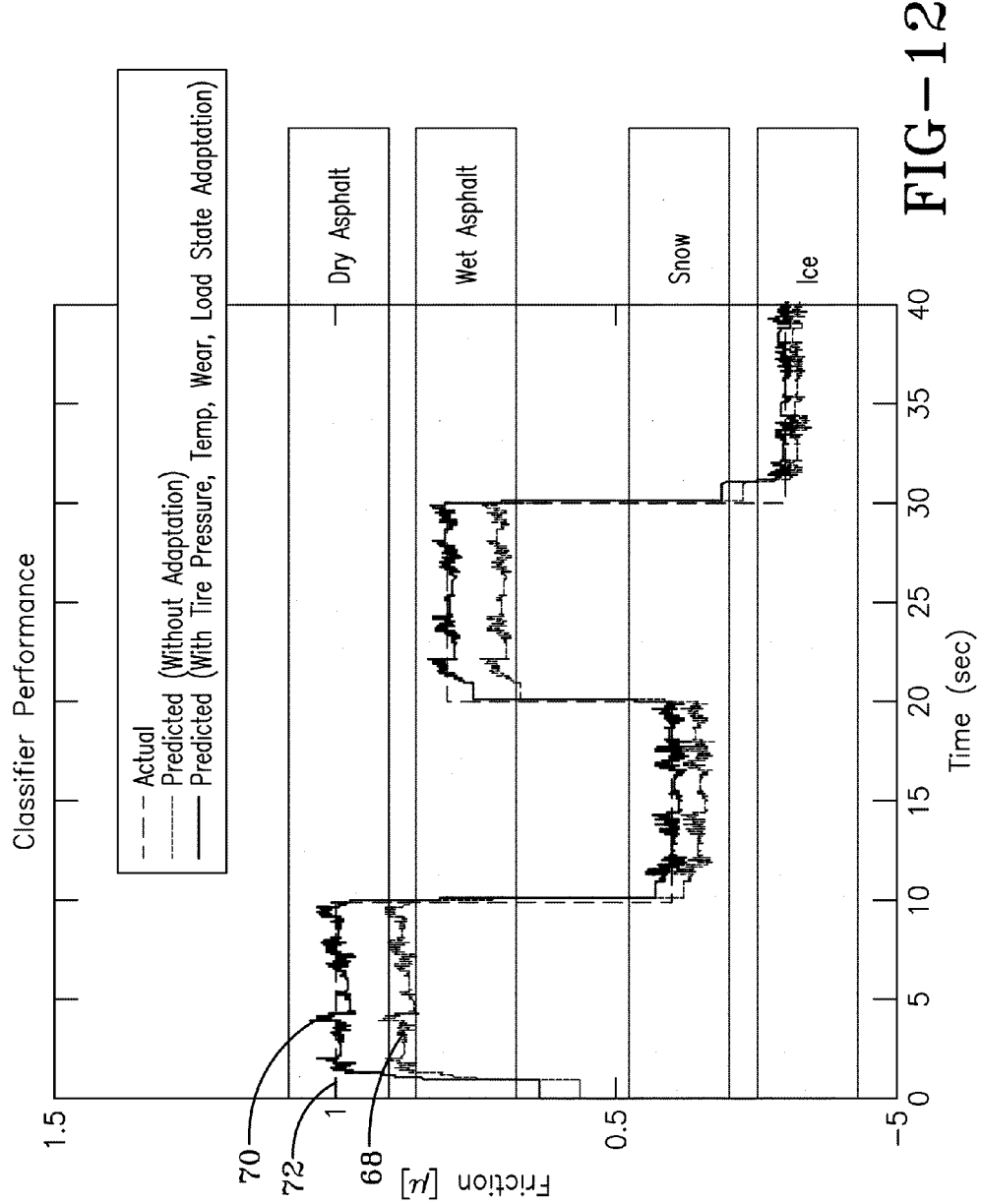
FIG. 12 is a graph of road surface classifier performance showing actual vs. predicted (with and without temperature state adaption) friction estimation comparison and showing the resultant misclassification (without temperature compensation).

The Road Surface Classifier performance is shown graphically in FIGS. 11 and 12. The performance of the RLS based Road Surface Classifier algorithm is evaluated with simulations where the road surface is designed to have sudden friction coefficient changes and the vehicle maneuver is straight driving with intermittent gas pedal presses. In FIG. 11, friction is plotted over time for actual, predicted (without adaptation) and predicted (with tire pressure, temperature, wear, load state adaptation). Performance of the road surface classifier was evaluated for a worn tire (2 mm tread) on different road surface conditions. Without the wear state adaptation scaling factor, slip slope based model overestimates the grip/friction level (see black dashed dotted line 62 in FIG. 11). This is due to the fact that, without adaptation, the increased longitudinal stiffness of the tire is incorrectly attributed to an increased road surface friction level when, in reality, the increased stiffness is due to a decrease in the tire tread depth (a worn tire having a higher stiffness). The adaptation model (see line 66) correctly compensates for this effect and estimates the grip level correctly in correlation to actual 64.

FIG. 12 demonstrates the Road Surface Classifier performance graphically for a hot tire (55° C.). In FIG. 12, friction is plotted over time for actual, predicted (without adaptation) and predicted (with tire pressure, temperature, wear, load state adaptation). Performance of the road surface classifier was evaluated for a worn tire (2 mm tread) on different road surface conditions. Without the temperature state adaptation scaling factor, slip slope based model overestimates the grip/friction level (see black dashed dotted line 68 in FIG. 11). This is due to the fact that, without adaptation, the decreased longitudinal stiffness of the tire is incorrectly attributed to a decreased road surface friction level when, in reality, the decreased stiffness is due to an increase in the tire temperature (a hotter tire having a lower stiffness). The adaptation model (see plotted line 70) correctly compensates for this effect and estimates the grip level correctly in correlation to actual 72.

It will be appreciated that tire-road friction coefficient information is of importance for vehicle dynamic control, such as yaw stability control, braking control, trajectory tracking control and rollover prevention. Existing tire-road friction coefficient estimation approaches require certain levels of vehicle longitudinal and/or lateral motion excitations (e.g. accelerating, decelerating, and steering) to satisfy the persistence of excitation condition for reliable estimations.

One approach taken in assessing friction is to estimate the longitudinal stiffness, i.e. the incline of the tire force relative to slip at low slips and from this value distinguish between different surface conditions. This method is more commonly known as the "slip-slope method" for friction coefficient estimation. Good estimations from this approach, however, in the low slip region are unpredictable.

The subject system and method uses adaption parameters in order to achieve a better tire-road friction estimation, including within the low slip region. Adaption parameters are used which govern tire longitudinal stiffness behavior in the low slip region and include inflation pressure, tread depth, normal loading and temperature. Using only the value of slip-slope itself cannot derive a maximum friction coefficient and is, accordingly, a less than satisfactory friction estimation solution.

The subject system and method utilizes tire-based attached sensor systems to compensate for dependencies such as pressure, temperature, wear state, tire construction. Consequently, the subject system and methodology can then isolate/alienate the effect of friction on the tire longitudinal stiffness. Using a tire attached TPMS sensor in conjunction with information from vehicle-based sensors compensates for the various operating conditions a tire experiences in real-world driving scenarios.

As a first step and as explained above, a longitudinal stiffness adaptation model is developed and implemented for generating a model-based tire longitudinal stiffness prediction under various operating conditions a tire experiences. The adaptation model uses scaling factors to account for the effects of load, inflation pressure, temperature, tire wear-state, and tire type (summer/winter/all season) on the tire longitudinal stiffness. The tire construction (tire ID), inflation pressure and temperature information is available from a tire-attached TPMS sensor module. The tire wear state and load information is available directly from tire attached sensors or indirectly from vehicle based sensors (suspension deflection for load and hub acceleration for wear state).

In parallel with the model-based estimation of longitudinal stiffness, an on-vehicle (real time) estimate of the tire longitudinal stiffness is made following a three-step estimation procedure:
(1) estimate the longitudinal tire force (using a sliding mode observer that relies on engine torque and brake torque measurements and wheel speed measurement available over the CAN bus of the vehicle);
(2) estimate the tire longitudinal slip ratio (using kinematic relationship);
(3) calculate the longitudinal stiffness (using a recursive least square algorithm with a forgetting factor).

Finally, an estimate of the tire road surface condition is made by comparing the model-based estimate of stiffness to the actual tire longitudinal stiffness measured on the vehicle. The proportioning factor between the model-based estimate and the actual longitudinal stiffness is a direct measure of the tire road friction coefficient ($\mu$).

It will be noted that the subject system and method develops real-time friction coefficient estimation algorithms based on slip-slope calculations for each tire rather than focusing on "average" friction coefficient for the vehicle. Accordingly, the subject system and method provides information about the individual wheel tire-road friction coefficients, a more valuable measurement for active safety systems than average vehicle-based friction measurements.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A tire-based system for estimating longitudinal stiffness between a tire and a road surface comprising:
at least one tire mounted to a wheel hub and supporting a vehicle;
load measurement means for determining a load level on the one tire;
wear estimation means for estimating a wear state of the one tire;
tire-based sensor input means for measuring tire-based input parameters;
longitudinal stiffness adaptation model means for deriving a longitudinal stiffness estimation scaled by the load level, the tire-based sensor input parameters, and the wear state.

2. The system of claim 1, wherein the tire-based sensor input parameters are at least one input from the group:
a measured air cavity pressure of the one tire;
tire-specific construction characteristics of the one tire;
a measured temperature of the one tire.

3. The system of claim 2, wherein the longitudinal stiffness adaptation model means algorithmically calculates the longitudinal stiffness estimation from inputs including the load level, the measured air cavity pressure of the one tire and the measured temperature of the one tire compensated by a wear state estimation of the one tire.

4. The system of claim 3, wherein the load level, measured air cavity pressure of the one tire and the measured temperature of the one tire comprise compensating scaling factors within the longitudinal stiffness adaptation model.

5. The system of claim 1, wherein the wear estimation means operably generates the wear state estimation for the one tire from a vehicle-measured acceleration of the wheel hub supporting the one tire.

6. The system of claim 5, wherein the wear estimation means operably generates the wear state estimation from a vertical acceleration of the wheel hub supporting the one tire.

7. A tire-based method for estimating longitudinal stiffness between a tire and a road surface comprising:
measuring a load level on at least one tire mounted to a wheel hub and supporting a vehicle;
estimating a wear state of the one tire;
measuring at least one tire-based sensor-derived compensating input parameter;
calculating a longitudinal stiffness estimation scaled by the load level, the at least one tire-based input, and the one tire wear state.

8. The method of claim 7, wherein the at least one tire-based sensor-derived input parameter is from the group:
a measured air cavity pressure of the one tire;
tire-specific construction characteristics of the one tire;
a measured temperature of the one tire.

9. The method of claim 8, wherein the step of calculating a longitudinal stiffness estimation includes algorithmically calculating the longitudinal stiffness estimation from a plurality of input parameters including the load level, the measured air cavity pressure of the one tire and the measured temperature of the one tire compensated by a wear state estimation of the one tire.

10. The method of claim 9, wherein the load level, measured air cavity pressure of the one tire, and the measured temperature of the one tire comprise compensating scaling factors within the step of calculating a longitudinal stiffness estimation.

11. The method of claim 7, wherein the step of estimating a wear state of the one tire includes generating the wear state estimation for the one tire from a vehicle-measured acceleration of a hub supporting the one tire.

12. The method of claim 11 wherein the step of estimating a wear state of the one tire includes operably generating the wear state estimation from a vertical acceleration of the wheel hub supporting the one tire.

* * * * *